US006808702B2

(12) United States Patent
Pasricha et al.

(10) Patent No.: US 6,808,702 B2
(45) Date of Patent: Oct. 26, 2004

(54) TREATMENT OF DISORDERS BY IMPLANTING STEM CELLS AND/OR PROGENY THEREOF INTO GASTROINTESTINAL ORGANS

(75) Inventors: Pankaj J. Pasricha, Houston, TX (US); Maria A. Micci, Dickinson, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 09/834,110

(22) Filed: Apr. 12, 2001

(65) Prior Publication Data

US 2002/0001578 A1 Jan. 3, 2002

Related U.S. Application Data

(60) Provisional application No. 60/196,806, filed on Apr. 13, 2000, and provisional application No. 60/232,301, filed on Sep. 12, 2000.

(51) Int. Cl.$^7$ .................. A01N 63/00; A01N 65/00; A61K 48/00
(52) U.S. Cl. .................. 424/93.1; 424/93.2; 424/93.21
(58) Field of Search .................. 424/93.1, 93.2, 424/93.21; 514/44

(56) References Cited

U.S. PATENT DOCUMENTS

| | | | |
|---|---|---|---|
| 5,175,103 A | 12/1992 | Lee et al. | |
| 5,753,491 A | 5/1998 | Major et al. | |
| 5,753,505 A | 5/1998 | Luskin | |
| 5,851,832 A | 12/1998 | Weiss et al. | |
| 5,869,463 A | 2/1999 | Major et al. | |
| 5,968,829 A | 10/1999 | Carpenter | |
| 5,980,885 A | 11/1999 | Weiss et al. | |
| 5,981,165 A | 11/1999 | Weiss et al. | |
| 6,025,157 A | 2/2000 | Klein et al. | |
| 6,497,872 B1 * | 12/2002 | Weiss et al. | ........... 424/93.1 |

FOREIGN PATENT DOCUMENTS

| | | |
|---|---|---|
| WO | WO 98/07841 | 2/1998 |
| WO | WO 99/67363 | 12/1999 |
| WO | WO 00/03001 | 1/2000 |

OTHER PUBLICATIONS

Keller et al. J Invest Surg 1997 Nov.–Dec.; 10(6):375–8 'Graft length affects outcome in fetal small bowel transplants'.*
Luo Y, et al. Xenotransplantation 1998 Aug;5(3):197–206 'Comparative histopathology of hepatic allografts and xenografts in the nonhuman primate'.*
Gage, "Mammalian Neural Stem Cells," *Science*. Feb. 25, 2000;287(5457):1433–8.
Hirka et al., "Differentiation of human embryonal carcinoma cells induces human immunodeficiency virus permissiveness which is stimulated by human cytomegalovirus coinfection," *J Virol*. May 1991;65(5):2732–5.

Pleasure et al., "NTera 2 cells: a human cell line which displays characteristics expected of a human committed neuronal progenitor cell." *J Neurosci Res*. Aug. 15, 1993;35(6):585–602.
Pleasure et al., "Pure, postmitotic, polarized human neurons derived from NTera 2 cells provide a system for expressing exogenous proteins in terminally differentiated neurons," *J Neurosci*. May 1992;12(5):1802–15.
Potten et al., "Stem cells: attributes, cycles, spirals, pitfalls and uncertainties. Lessons for and from the crypt," *Development*. Dec. 1990;110(4):1001–20.
Srinivas et al., "Dominant effects of RET receptor misexpression and ligand–independent RET signaling on ureteric bud development," *Development*, Apr. 1999;126(7): 1375–86.
Smithies et al., "Insertion of DNA sequences into the human chromosomal beta–globin locus by homologous recombination," *Nature*. Sep. 19–25, 1985; 317(6034):230–4.
"Stem Cells: A Primer," National Institutes of Health, Office of the Director [online] United States, [retrieved Apr. 4, 2001]. Retrieved from the Internet:<URL:http://www.nih.gov/news/stemcell/primer.htm>, 6 pages.
Taraviras et al., "Signalling by the RET receptor tyrosine kinase and its role in the development of the mammalian enteric nervous system," *Development*. Jun. 1999;126(12): 2785–97.
Wertkin et al., "Human neurons derived from a teratocarcinoma cell line express solely the 695–amino acid amyloid precursor protein and produce intracellular beta–amyloid or A4 peptides," *Proc Natl Acad Sci U S A*. Oct 15, 1993;90(20):9513–7.
Younkin et al., "Inducible expression of neuronal glutamate receptor channels in the NT2 human cell line," *Proc Natl Acad Sci U S A*. Mar. 15, 1993;90(6):2174–8.
Zheng et al., "Fidelity of targeted recombination in human fibroblasts and murine embryonic stem cells," *Proc Natl Acad Sci U S A*. Sep. 15, 1991;88(18):8067–71.
Cornelius et al., "In Vitro–Generation of Islets in Long–Term Cultures of Pluripotent Stem Cells From Adult Mouse Pancreas," *Hormone and Metabolic Research*, 1997, 29(6):271–277.
Micci et al., "Successful Transplantation of Neuronal Stem Cells in the Gastrointestinal Tract with Evidence of Morphological and Functional Differentiation," *Gastroenterology*, vol. 118, No. 4, Apr. 2000. Abstract No. 1194.

(List continued on next page.)

*Primary Examiner*—Joseph Woitach
(74) *Attorney, Agent, or Firm*—Mueting, Raasch & Gebhardt, P.A.

(57) ABSTRACT

A method of treating a disorder, typically a gastrointestinal disorder, that includes implanting stem cells and/or progeny thereof into a gastrointestinal organ of a subject. Also, a method of producing enhanced levels of insulin that includes implanting stem cells and/or progeny thereof into the pancreas of a subject.

17 Claims, 5 Drawing Sheets

OTHER PUBLICATIONS

Micci et al., "Successful Transplantation of Neuronal Stem Cells in the Gastrointestinal Tract with Evidence of Morphological and Functional Differentiation," *Society for Neuroscience Abstracts*, vol. 26, No. 1–2, Nov., 2000. Abstract No. 327.10.

Micci et al., "Neural Stem Cells Express RET, Produce Nitric Oxide, and Survive Transplantation in the Gastrointestinal Tract," *Gastroenterology*, Oct., 2001, 121:757–766.

Scheffold et al., "Purified Allogeneic Hematopoietic Stem Cell Transplantation prevents Autoimmune Diabetes and Induces Tolerance to Donar Matched Eslets," *Blood*, vol. 94, No. 10, Nov. 15, 1999. Abstract No. 2947.

Yang et al., "In vitro trans–differentiation of adult hepatic stem cells into pancreatic endocrine hormone–producing cells," *PNAS*, Jun. 11, 2002; 99(12):8078–8083.

* cited by examiner

MW
(KDa)
200 > — — < nNOS
117 >
97 >

205 —
120 — ← Ret
84 —

+ NSC

GFRα1 →

TREATMENT OF DISORDERS BY IMPLANTING STEM CELLS AND/OR PROGENY THEREOF INTO GASTROINTESTINAL ORGANS

This application claims the benefit of U.S. Provisional Application Ser. No. 60/196,806, filed Apr. 13, 2000, and U.S. Provisional Application Serial No. 60/232,301, filed Sep. 12, 2000, which are incorporated herein by reference in its entirety.

BACKGROUND

Degeneration of specific types of neurons in the central nervous system (CNS) or the enteric nervous system (ENS) results in several major disorders. In Parkinson's disease (PD), dopaminergic neurons are lost in the substanita nigra of the brain, leading to impairment of coordination of skeletal muscle movement. It has been demonstrated that there is a loss of dopaminergic neurons in the colon of PD patients with constipation. In achalasia, Hirschsprung's disease, and congenital pyloric stenosis, loss of nitric oxide-producing neurons (nitrinergic) is well documented. This nitrinergic loss leads to the inability of the gastrointestinal (GI) smooth muscle to relax, resulting in severe motility disorders.

An exciting new strategy of treatment is to replace these losses by implanting neurons into the affected areas. For example, implantation of fetal neurons into the brain of PD patients has resulted in the improvement of motor function. However, anatomical and functional contacts of these implanted cells with striatal neurons could not be clearly demonstrated because of difficulty in identifying the implanted neurons and because no functional assay for connectivity was available. Use of fetal tissue has severe limitations. The supply of human fetal tissue is restricted and a potential exists for host/graft rejection of the implanted neurons.

Neurodegenerative disorders of the CNS, such as PD, Alzheimer's disease, multiple sclerosis, and Huntington's disease are common problems in clinical practice. Besides the well-known enteric nervous degenerative disorders such as achalasia, Hirschsprung's disease, and congenital pyloric stenosis, several other common gastrointestinal disorders, e.g., reflux disease, irritable bowel syndrome, and intestinal pseudo-obstruction are increasingly recognized as related to disordered enteric neurons.

The enteric nervous system (ENS) is apart of the peripheral nervous system and consists of neuronal cell bodies, their fibers, and supporting cells located within the wall of the GI tract. These cell bodies are arranged in two major ganglionated plexuses, a peripheral myenteric (Aucibach's) between the circular and the longitudinal muscle layers, and a submucosal (Meissner's) plexus in the submucosal connective tissue between tire muscularis mucosa and circular muscle. For the most part, the myenteric neurons provide excitatory (acetylcholine and substance P) and inhibitory (nitric oxide, VIP, CORP, and ATP) transmitters to the gut smooth muscle. The tone of the gut muscle depends on the summated influence of the opposing actions of these neurotransmitters.

Current treatment options for neurodegenerative gastrointestinal disorders are very limited. Thus, there is a need for new treatment protocols for gastrointestinal disorders that involve neurons, muscle tissue, or other tissues, as well as other disorders that are related to gastrointestinal organs.

SUMMARY

The present invention is directed to a method for the treatment of disorders using stem cells and/or progeny thereof for implantation into a gastrointestinal organ of a subject (preferably, a mammal, and more preferably, a human). The spectrum of disorders in which such treatment will be useful includes, but is not limited to, degenerative, immunologic/inflammatory, neoplastic, and idiopathic conditions of the gastrointestinal tract that may be either congenital or acquired. Thus, the disorders include any of a variety of gastrointestinal disorders that involve, for example, neurons as well as muscle tissue, although other tissues can be involved as well. Other disorders that are related to the function or dysfunction of a gastrointestinal organ can also be treated using the method of the present invention.

Gastrointestinal organs include hollow and solid organs. Hollow gastrointestinal organs include those that make up the alimentary tract, such as the mouth, esophagus, stomach, and bowels. Solid gastrointestinal organs include those that drain into the gastrointestinal alimentary tract, such as the liver, gall bladder, and pancreas.

As used herein, treating a gastrointestinal disorder includes both therapeutic and prophylactic (i.e., preventive) treatment. The success of such a treatment can be determined by evaluation of the functional status of an organ or a patient as determined by clinical outcome and/or morphological analysis.

Specifically, the present invention provides a method of implantation (e.g., transplantation) of stem cells (preferably, multipotent or totipotent stem cells) into a gastrointestinal organ (e.g., the gastrointestinal alimentary tract or solid organs that drain into the alimentary tract) for purposes of repopulating various cellular components (such as the neurons, muscles, or other cell types) and/or providing a source of biological material (e.g., neurotransmitters, cytokines, anticytokines, growth factors, immune modulators, antiinflammtory agents, antineoplastic agents, analgesics, etc.) for therapeutic intent. The source of these stem cells can be embryonic or adult neural and non-neural tissue (e.g., bone marrow or fat tissue).

The implantation can be carried out via local injection, as for example into a wall of the gastrointestinal tract or into a solid gastrointestinal organ such as the pancreas or liver, by administration into the systemic (e.g., via the blood stream or the peritoneal cavity) or portal circulation system, or by any other practical means.

The present invention also provides a method of producing enhanced levels of insulin in a patient. This involves implanting stem cells and/or progeny thereof into the pancreas, which is considered a gastrointestinal organ as used herein because it is a solid organ that drains into the gastrointestinal alimentary tract.

BRIEF DESCRIPTION OF THE DRAWINGS

FIG. 2. (A) Western blot analysis of rat neural stem cells total protein extract. (B) nNOS immunoreactivity in rat neural stem cells.

FIG. 3. (A) Pseudocolor images of NO production after stimulation by ionomycin (1.4 $\mu$M) in cultured neural stem cells in the presence of L-arginine (1 mM) or L-NAME (100 $\mu$M). NSCs were loaded with the NO-sensitive fluorescent indicator DAF-2 and cells were viewed with a confocal laser-scanning microscope system, utilizing an argon-ion laser (488 nm) coupled to an inverted Nikon Diaphot microscope. (B) Relative fluorescence intensity changes reflecting NO production in 11 cultured neural stem cells measured in the presence of L-arginine (1 mM) or L-NAME (100 μM). Error bars indicate SD. * p<0.05; ** p<0.01 (paired Student's t-test).

FIG. 4. (A) DiI-labelled NSCs 8 weeks after transplantation in the pylorus of wild C57BL/6J mice. (B) Double immunofluorescence staining of grafted DiI-labelled NSCs showing colocalization of β-tubulin and nNOS (arrows). LM=longitudinal muscle; CM=circular muscle FIG. 5. (A) Western blot analysis of rat neural stem cells total protein extract. (B) Ret immunoreactivity in rat neural stem cells. Cell nuclei are counterstained in blue (represented by the light areas) as with DAPI (4,6-diamidino-2-phenylindole-dihydrochloride). Scale bars=10 μm.

FIG. 6. (A) Western blot analysis of rat neural stem cells total protein extract (NSC)+positive control. (B) GFRα1 immunoreactivity in rat neural stem cells. (C) GFRα2 immunoreactivity in rat neural stem cells. Cell nuclei counterstained in blue (represented by the light areas) with DAPI. Scale bars=10 μm.

FIG. 7. Ret immunoreactivity in rat neural stem cells that were exposed for 10 days to either neurobasal media as control (A) or GDNF, 100 ng/ml (B) Cell nuclei are counterstained in blue (represented by the light areas) with DAPI. Note the spheroid formation in B. Scale bars=50 μm. (C) Graph shows significant expansion in RET$^+$ cell population under the effects of GDNF at the same concentration.

DETAILED DESCRIPTION OF PREFERRED EMBODIMENTS

The present invention is directed to a method for the treatment of gastrointestinal disorders using stem cells and/or progeny thereof for implantation into a gastrointestinal organ. Specifically, the present invention provides a method of implantation (e.g., transplantation) of stem cells (e.g., multipotent, totipotent, or pluripotent stem cells) or progeny thereof into a gastrointestinal organ (preferably, the gastrointestinal alimentary tract) for purposes of repopulating various cellular components (such as the neurons, muscles, or other cell types) and/or providing a source of biological material for therapeutic intent.

The spectrum of disorders in which such therapy will be used includes degenerative, immunologic/inflammatory, neoplastic, and idiopathic conditions of the gastrointestinal tract that may be either congenital or acquired. Examples include, but are not limited to, achalasia, gastrophoresis, intestinal pseudo obstruction, and Hirschsbrung's disease. Preferably, the gastrointestinal disorders can be any of a variety of disorders that involve, for example, neurons as well as muscle tissue or other cell types of the gastrointestinal tract. Further, this invention can also be used to provide therapy for disorders that are not traditionally considered gastrointestinal disorders but are related to organs that are considered gastrointestinal organs (e.g., liver, gall bladder, and pancreas) in that the organs drain into the gastrointestinal alimentary canal. Such disorders include diabetes, which can be treated by means of implantation of stem cells into the pancreas of a patient to cause enhancement of insulin production.

The source of the stem cells can be embryonic or adult neural and non-neural tissue. Generally, the term "neural stem cell" is used loosely to describe cells that: (i) can generate neural tissue or are derived from the nervous system; (ii) have some capacity for self-renewal; and (iii) can give rise to cells other than themselves through asymmetric cell division. An important identifying feature of a stem cell is its ability to exhibit self-renewal or to generate more of itself. The simplest definition of a stem cell is a cell with the capacity for self-maintenance. A more stringent (but still simplistic) definition of a stem cell is provided by Potten and Loeffler (*Development*, 110, 1001, (1990)) who have defined stem cells as "undifferentiated cells capable of a) proliferation, b) self-maintenance, c) the production of a large number of differentiated functional progeny, d) regenerating the tissue after injury, and e) a flexibility in the use of these options." The role of stem cells is to replace cells that are lost by natural cell death, injury, or disease. The presence of stem cells in a particular type of tissue usually correlates with tissues that have a high turnover of cells. However, this correlation may not always hold, as stem cells are thought to be present in tissues (e.g., liver) that do not have a high turnover of cells.

The capability of a cell to divide without limit and produce daughter cells which terminally differentiate into neurons and glia are stem cell characteristics. Accordingly, as used herein, a stem cell is capable of self-maintenance, meaning that with each cell division, one daughter cell will also be a stem cell. The non-stem cell progeny of a stem cell are termed progenitor cells. The progenitor cells generated from a single multipotent neural stem cell are capable of differentiating into neurons, astrocytes (type I and type II) and oligodendrocytes. Some progenitor cells can produce progeny that are capable of differentiating into more than one cell type. For example, an O-2A cell is a glial progenitor cell that gives rise to oligodendrocytes and type II astrocytes, and thus could be termed a "bipotential" progenitor cell. A distinguishing feature of a progenitor cell is that, unlike a stem cell, it has limited proliferative ability and thus does not exhibit self-maintenance.

Stem cells from neural and other tissues are often defined by their tissue of origin. Alternatively, they can be defined by their potentiality (Gage, *Science*, 287, 1433–1438 (2000)). Understanding the potentiality of a cell is best described in the context of normal human development. As described in Stem Cells: A Primer, *National Institutes of Health*, May 2000 can be found on the Internet at nih.gov/news/stemcell/primer.htm, human development begins when a sperm fertilizes an egg and creates a single cell that has the potential to form an entire organism. This fertilized egg is totipotent, meaning that its potential is total. In the first hours after fertilization, this cell divides into identical "totipotent" cells. This means that either one of these cells, if placed into a woman's uterus, has the potential to develop into a fetus. In fact, identical twins develop when two totipotent cells separate and develop into two individual, genetically identical human beings. Approximately four days after fertilization and after several cycles of cell division, these totipotent cells begin to specialize, forming a hollow sphere of cells, called a blastocyst. The blastocyst has an outer layer of cells and inside the hollow sphere, there is a cluster of cells called the inner cell mass.

The outer layer of cells will go on to form the placenta and other supporting tissues needed for fetal development in the uterus. The inner cell mass cells will go on to form virtually all of the tissues of the human body. Although the inner cell mass cells can form virtually every type of cell found in the human body, they cannot form an organism because they are unable to give rise to the placenta and supporting tissues necessary for development in the human uterus. These inner cell mass cells are "pluripotent." This means that they can give rise to many types of cells but not all types of cells necessary for fetal development. Because their potential is not total, they are not totipotent and they are not embryos. Thus, if an inner cell mass cell were placed into a woman's uterus, it would not develop into a fetus (Stem Cells: A Primer, *National Institutes of Health*, May 2000 can be found on the Internet at nih.gov/news/stemcell/primer.htm).

The pluripotent stem cells undergo further specialization into stem cells that are committed to give rise to cells that have a particular function. Examples of this include blood stem cells which give rise to red blood cells, white blood cells and platelets; and skin stem cells that give rise to the various types of skin cells. These more specialized stem cells are called "multipotent" (Stem Cells: A Primer, *National Institutes of Health*, May 2000 can be found on the Internet at nih.gov/news/stemcell/primer.htm).

Most stem cells fall into the category of multipotent stem cells. Multipotent stem cells can be obtained from embryonic, post-natal, juvenile, or adult tissue. The tissue can be obtained from a wide variety of animals, such as insects, fish, reptiles, birds, amphibians, mammals, and the like. The preferred source is from mammals, preferably rodents and primates, and most preferably, mice and humans. In the case of a heterologous donor animal, the animal may be euthanized, and the tissue (e.g., neural tissue) and specific area of interest removed using a sterile procedure. Areas of particular interest, for example, include any area from which neural stem cells can be obtained (e.g., any part of the nervous system, bone marrow, etc.).

Non-neural stem cells can be obtained from anywhere in the body as well as embryonic stem cells. Stem cells can be derived from more primitive cells that have the capacity to generate neural stem cells and non-neural stem cells (i.e., stem cells of other tissues).

Stem cells can be obtained from donor tissue by dissociation of individual cells from the connecting extracellular matrix of the tissue. Tissue from a particular region is removed using a sterile procedure, and the cells are dissociated-using any method known in the art including treatment with enzymes such as trypsin, collagenase and the like, or by using physical methods of dissociation such as with a blunt instrument.

The stem cells can be cultured in suspension or on a fixed substrate. However, substrates tend to induce differentiation of the stem cell progeny. Thus, suspension cultures are preferred if large numbers of undifferentiated stem cell progeny are desired. Suitable culture media capable of supporting cell growth include HEM, DMEM, RPMI, F-12, and the like, which can contain supplements required for cellular metabolism such as glutamine and other amino acids, vitamins, minerals and useful proteins such as transferrin, and the like. The culture medium may also contain antibiotics to prevent contamination with yeast, bacteria, and fungi, such as penicillin, streptomycin, gentamicin, and the like. Conditions for culturing should be close to physiological conditions (preferably, a pH of about 6 to about 8, and a temperature of about 30° C. to about 40° C.). The culture medium can be supplemented with at least one proliferation-inducing growth factor, such as EGF, amphiregulin, acidic fibroblast growth factor (aFGF or FGF-1), basic fibroblast growth factor (bFGF or FGF-2), transforming growth factor alpha (TGF-alpha), and combinations thereof. In addition to proliferation-inducing growth factors, other growth factors may be added to the culture medium that influence proliferation and differentiation of the cells including NGF, platelet-derived growth factor (PDGF), thyrotropin releasing hormone (TRH), and the like.

Additionally, the stem cells, once they have proliferated in vitro, could also be genetically modified in vitro using known techniques. The in vitro genetic modification may be more desirable in certain circumstances than in vivo genetic modification techniques when more control over the infection with the genetic material is required. Stem cell progeny can be cryopreserved until they are needed by any method known in the art. The cells can be suspended in an isotonic solution, preferably a cell culture medium, containing a particular cryopreservant. Such cryopreservants include dimethyl sulfoxide (DMSO), glycerol, and the like.

A wide variety of genetic modifications of the cells is within the scope of the present invention. For example, the cells can be genetically modified to express growth factors and other types of neurological agents such as neurotransmitters. When the genetic modification is for the production of a biologically active substance, the substance will generally be one that is useful for the treatment of a given gastrointestinal disorder. For example, it may be desired to genetically modify cells so they produce nitric oxide (for achalasia). Cells can also be modified in vivo to express growth factor receptors, neurotransmitters or their receptors, neurotransmitter-synthesizing genes, neuropeptides, and the like.

The stem cells and/or progeny thereof can be administered to a host in a wide variety of ways. The implantation (e.g., transplantation) can be carried out via local injection, for example, into the wall of the gastrointestinal tract, by administration into the systemic or portal circulation system, or by any other practical means. The use of stem cells in the treatment of disorders such as gastrointestinal disorders can be demonstrated by the use of animal models.

The instant invention allows the use of stem cells and/or stem cell progeny prepared from donor tissue which is xenogeneic to the host. In general, however, in order for xenografts to be successful it is preferred that some method of reducing or eliminating the immune response to the implanted tissue be employed. Thus, recipients will often be immunosuppressed, either through the use of immunosuppressive drugs such as cyclosporin, or through local immunosuppression strategies employing locally applied immunosuppressants.

As an alternative to employing immunosuppression techniques, methods of gene replacement or knockout using homologous recombination in embryonic stem cells (as taught by Smithies et al., *Nature,* 317, 230–234 (1985)), and extended to gene replacement or knockout in cell lines (H. Zheng et al., *PNAS,* 88, 8067–8071 (1991)), can be applied to stem cells for the ablation of major histocompatibility complex (MHC) genes. Stem cells lacking MHC expression would allow for the grafting of enriched neural cell populations across allogeneic, and perhaps even xenogeneic, histocompatibility barriers without the need to immunosuppress the recipient.

Cells can be delivered throughout any affected area, in particular in a site-specific manner (i.e., locally) or systemically. Cells can be administered to the particular region using any method that maintains the integrity of surrounding areas, preferably by local injection. Cells can also be administered to the systemic or portal circulation system.

In addition to stem cells or progeny thereof, pharmaceutical compositions useful for the methods of the present invention can include growth factors to promote growth and differentiation of stem cells, immunosuppresants, antiinflammatory agents, etc. Additionally, if desired, stem cells or progeny thereof can be encapsulated, as is well known to one of skill in the art.

Survival of the graft in the living host can be examined using various methods including clinical, radiological, histological, physiological, etc. Non-invasive scans can be used, including computerized axial tomography (CAT scan or CT scan), nuclear magnetic resonance or magnetic resonance imaging (NMR or MRI), or positron emission tomography (PET) scans. Post-mortem examination of graft survival can be done by removing tissue, and examining the affected region macroscopically, or more preferably using microscopy. Cells can be stained with any stains visible under light or electron microscopic conditions, more particularly with stains that are specific for neurons and glia. Particularly useful are monoclonal antibodies that identify neuronal cell surface markers such as the M6 antibody which identifies mouse neurons. Most preferable are antibodies that identify any neurotransmitters, particularly those directed to GABA, TH, ChAT, and substance P, and to enzymes involved in the synthesis of neurotransmitters, in particular, GAD. Transplanted cells can also be identified by prior incorporation of tracer dyes such as rhodamine- or fluorescein-labeled microspheres, fast blue, bisbenzamide or retrovirally introduced histochemical markers such as the lac Z gene, which produces beta galactosidase.

EXAMPLES

The following examples are given to illustrate specific preferred embodiments of the present invention. Numerous other variations, however, are within the scope of the present invention.

Generation and in vitro culture of rat forebrain neural stem cells. Neural stem cells were obtained from staged-pregnant female Holtzman rats at embryonic day 17. The brains of embryonic rats were removed and the subventricular zone tissue (SVZ) was dissected from each brain hemisphere. Single cell suspensions were then made from this tissue using dispase/DNAse treatment and gentle trituration. The fractions were combined, pelleted and resuspended in Neurobasal medium. After 2–4 hours, the cells were spun down and media replaced with NB27 (Neurobasal medium containing B27 and antibiotics) plus 20 nanograms per milliliter (ng/ml) bFGF and 20 ng/ml EGF. Fifty-percent of the culture media was replaced on a daily basis.

Co-immunoprecipitation and Western blotting. Total protein extract was obtained from neural stem cells by lysing the cells in a solution containing 5% (sodium dodecyl sulfate) SDS, 1 millimolar (mM) benzamidine, 0.5 mM phenylmethyl-sulpfonyl fluoride, 1 mM ethylenediaminetetraacetic acid (EDTA) in Tris-buffered saline (TBS) (50 mM Tris-HCl [pH 7.5], 150 mM NaCl). Insoluble material was removed by centrifugation at 13,000×g for 10 minutes (min.). For co-immunoprecipitation, 500 microgram ($\mu$g) of protein from whole cell lysates was incubated with either 2 microliter ($\mu$l) of an anti-Ret antibody (sc-167-G, Santa Cruz Biotechnology, Santa Cruz, Calif.) and 20 $\mu$l of protein A-agarose (Boehringer Mannheim, Indianapolis, Ind.) at 4° C. overnight. Precipitated aggregates were resuspended in Laemmli's sample buffer and run on 7.5% SDS-PAGE gels, transferred to PVDF membranes (Amersham, Amersham Place, UK). They were incubated with either anti-RET tyrosine kinase receptor (Ret) antibody at a dilution of 1/1000 in 5% dry milk, 0.05% Tween 20 in TBS for 2 hours at room temperature. After the incubation with an horseradish peroxidase (HRP)-conjugated secondary antibody, the immunoreactivity was detected by enzyme catalyzed luminescent (ECL) kit (Amersham). For a negative control, the samples were treated in the same manner as described above except the omission of the primary antibody in immunoprecipitation.

Immunocytochemistry. For immunocytochemistry, neural stem cells were seeded onto poly-ornithine-coated chambered slides (Nunc, Naperville, Ill.) or on a monolayer of human intestinal smooth muscle (purchased from ATCC. Cells were fixed with 100% methanol for 10 minutes at −20° C. The following antibodies were used: anti-βIII-tubulin (0.5 $\mu$g/ml; Promega Corp., Madison, Wis.) and anti-nNOS (1:200 dilution; Santa Crux Biotechnology, Santa Cruz, Calif.). Prior to incubations with primary antibodies, cells were blocked with 5% normal goat serum for 1 hour at room temperature. Cells were washed in phosphate buffer solution (PBS) and incubated with primary antibodies diluted in PBS containing 1.5% goat serum, overnight at 4° C. Cells were then incubated with the appropriate Alexa-conjugated secondary antibody (Alexa-488; Alexa-594: diluted 1:500, Molecular Probes, Eugene, Oreg.) for 1 hour at room temperature. Proper controls were produced by omitting the primary antibodies.

Nitric oxide detection. Neural stem cells were plated onto poly-ornithine-coated glass coverslips. The cells were incubated for 1 hour at 37° C. in standard Krebs solution containing the NO-sensitive fluorescent indicator DAF-2 DA (10 $\mu$M, Alexis Biochemicals, San Diego, Calif.). After loading, the cells were washed in Krebs and placed in Krebs containing L-arginine or L-NAME. The cells were viewed with a confocal laser-scanning microscope system, utilizing an argon-ion laser (488 nm) coupled to an inverted Nikon Diaphot microscope.

Labeling methods and preparation of cells for transplantation. To enable the detection of the cells in vivo, neural stem cells were labeled with CM-DiI (Molecular Probes, Eugene, Oreg.) according to manufacturer instructions. After washing in PBS, the cells were resuspended in PBS at a concentration of 400,000 cells/$\mu$l and kept on ice. For transplantation, male C57BL/6J wild-type mice (Jackson Laboratories) weighing ~20 gm were used. Surgery was performed under deep anesthesia. Mice received 2 $\mu$l cell suspension bilaterally into the pylorus using a 22G needle attached to a 10 $\mu$l Hamilton syringe.

Tissue processing. At 2, 4, and 8 weeks after transplantation mice were anesthetized and transcardially perfused and fixed with ice-cold 4% paraformaldehyde (PFA) in 0.1M PBS. The pylorus was removed, post-fixed in PFA for 1 h at room temperature and cryoprotected in 30% sucrose in PBS overnight at 4° C. The tissue was then embedded in optimal cutting compound (OCT) and 15–30 $\mu$m frozen sections were cut on a cryostat and collected for further processing. For double-immunofluorescence, sections were permeabilized with 50% glycerol/50% PBS to allow penetration of the antibodies. Colocalization of flourescent lipophilic dye DiI with these markers was conducted by confocal microscopy, using an OZ model confocal microscope (Noran Intruments) coupled to an inverted Nikon Diaphot microscope.

Figure 1:
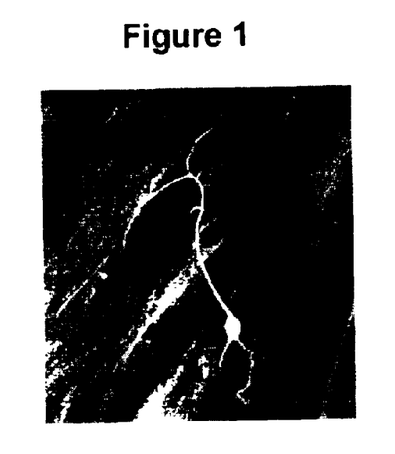
FIG. 1. A neural stem cell (stained for the neuronal marker β-tubulin) in co-culture with human intestinal smooth muscle cells.

Results and Discussion. Experiments have demonstrated that neural stem cells (NSCs) isolated from rat forebrain can form anatomical contact with intestinal smooth muscles in vitro (FIG. 1).

Figure 2A:
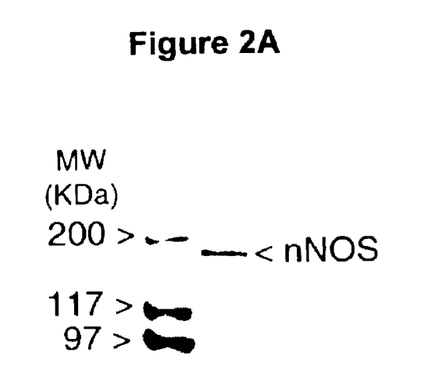
Figure 2B:
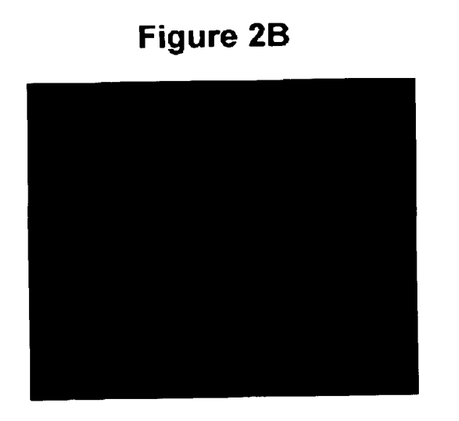
Figure 3A:
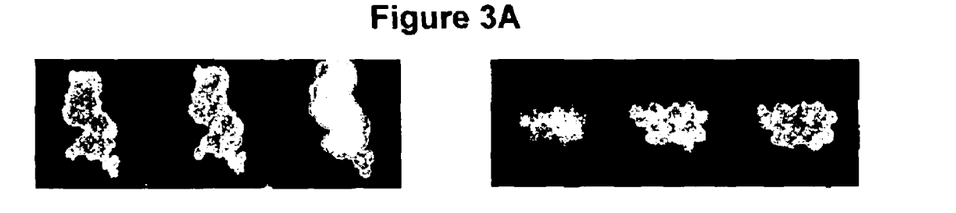
Figure 3B:
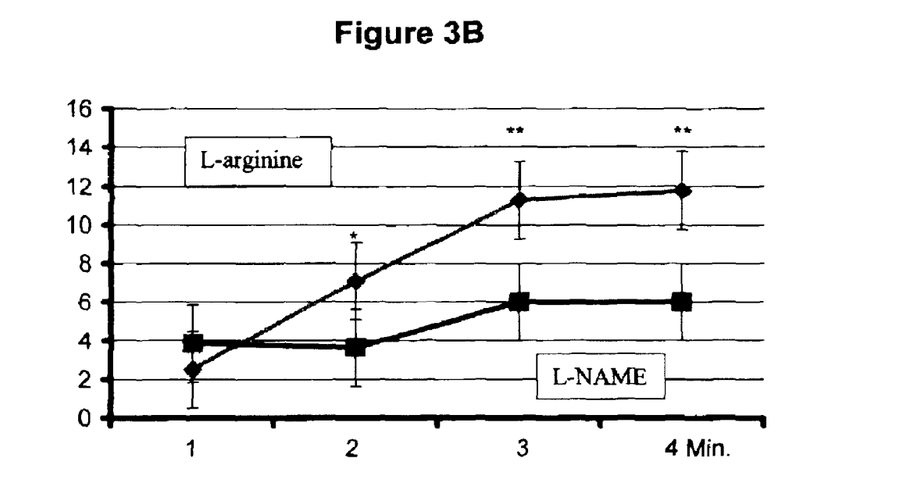

Cultured NSCs also express neuronal nitric oxide (nNOS) and produce nitric oxide (NO) in vitro (FIG. 2), indicating that the use of NSCs is a valid tool to reintroduce nNOS in experimental conditions where there is a functional lack of such enzyme.

Figure 4A:
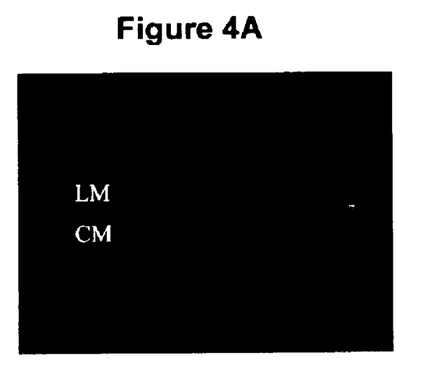
Figure 4B:
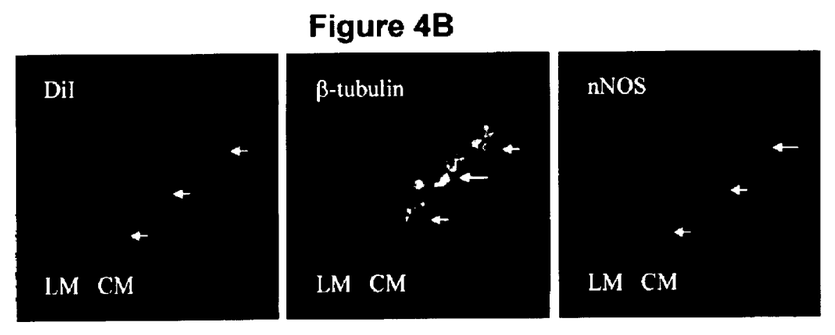
Figure 5A:
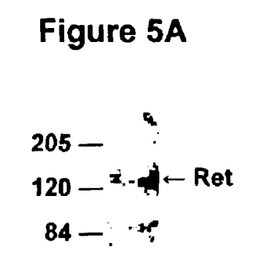
Figure 5B:
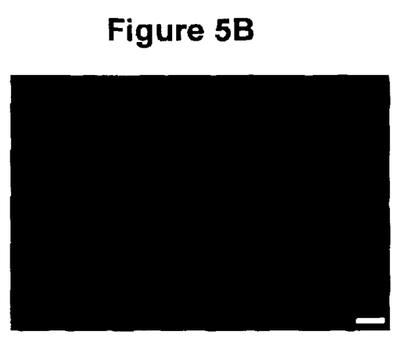

Data has shown that NSCs can be successfully implanted into the gastrointestinal wall of wild type mice (FIG. 3) and that they differentiate into nitrinergic neurons (expressing NNOS) 2 weeks after transplantation (FIG. 4). NSCs are still viable and NNOS immunoreactive 8 weeks after transplantation (data not shown).

Figure 6A:
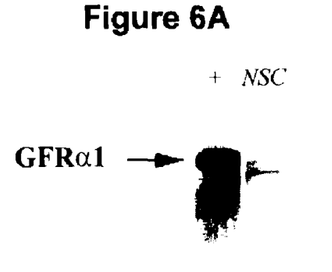
Figure 6B:
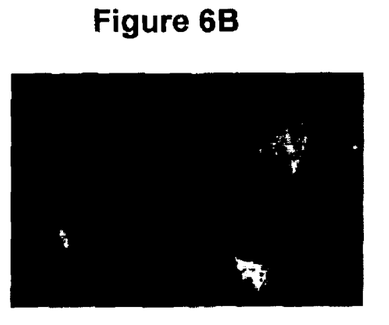
Figure 6C:
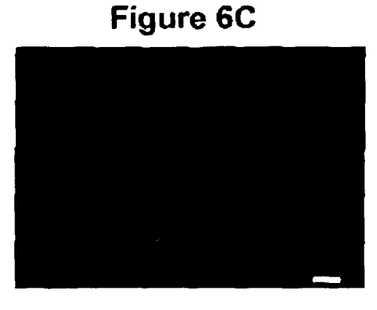
Figure 7A:
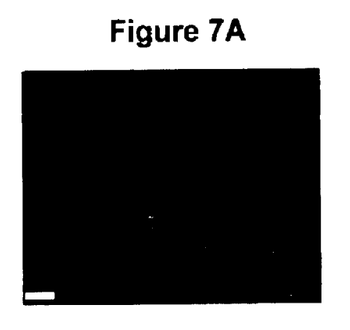
Figure 7B:
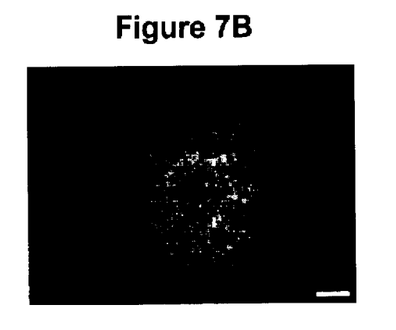
Figure 7C:
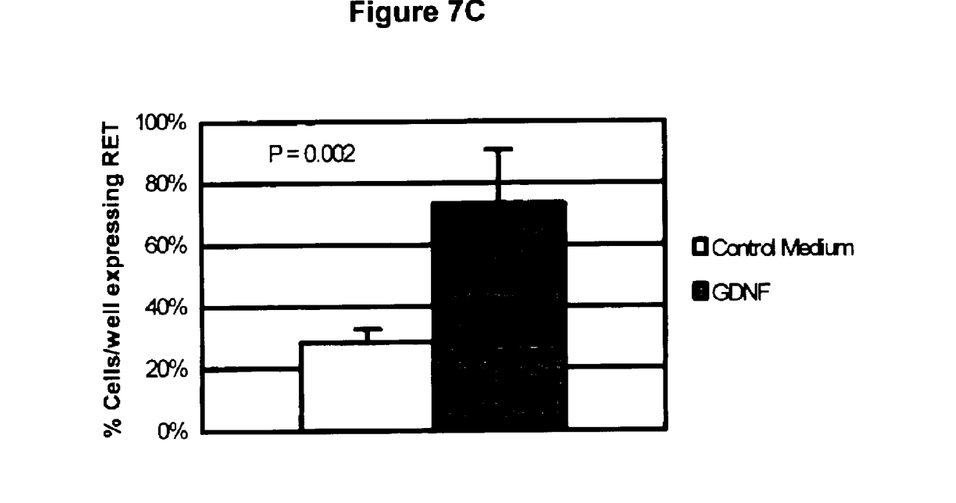

The ENS, like other peripheral neuronal systems, is derived entirely from the neural crest. Crest-derived progenitors are pluripotential and can successfully innervate any region of the gut; it is the micro-environment within the gut wall that appears to be important in determining regional specialization and differentiation of these cells. Interaction of the RET tyrosine kinase receptor expressed by these cells with gut-derived neurotrophic growth factors, GDNF (glial cell line derived growth factor) and neurturin (NTN) (FIG. 5) is important in this process. This interaction also involves a set of extracellular GPI-linked receptors, closely linked to RET: the GDNF family receptor (GFR) $\alpha 1$ and $\alpha 2$ (FIG. 6). GDNF acts as a mitogen for these precursors until about E12, resulting in an expansion of their number sufficient to colonize the entire bowel (FIG. 7). Later, it serves as a differentiation factor, promoting the development of neurons at the expense of glia.

NTN is also an important enteric neurotrophin and promotes the proliferation and survival of neuroglial precursors in vitro, although not as important as RET as shown by mutations of NTN or its preferred receptor, GFR$\alpha 2$. It is postulated that the NTN/GFR$\alpha 2$ system is important for maintenance of the mature enteric nervous system while the GDNF/GFR$\alpha 1$ system is important for its development.

The above studies in our laboratory have demonstrated that neural stem cells (NSC) isolated form the rat forebrain express the receptor system for the enteric neurotrophin GDNF and NTN.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims. The complete disclosures of all patents, patent documents, and publications listed herein are incorporated by reference, as if each were individually incorporated by reference.

What is claimed is:

1. A method of providing a nitric oxide (NO) within the gastrointestinal alimentary tract of a subject suffering from a gastrointestinal disorder associated with lower levels of NO comprising implanting isolated embryonic neural stem cells directly into the gastrointestinal alimentary tract of the subject, wherein the implanted embryonic neural stem cells produce NO.

2. The method of claim 1 wherein the implanted cells repopulate neurons.

3. The method of claim 1 wherein the subject suffers from a disorder of the enteric nervous system.

4. The method of claim 1 wherein the gastrointestinal alimentary tract is the mouth, the esophagus, the stomach, or the bowels.

5. The method of claim 1 wherein implanting cells into a gastrointestinal alimentary tract of a subject comprises administering the cells by local injection.

6. The method of claim 1 wherein the implanted neural stem cells further produce substance P.

7. The method of claim 1 wherein the neural stern cells are implanted into the pylorus.

8. The method of claim 1 wherein the neural stem cells are implanted into the duodenum.

9. The method of claim 1 wherein said gastrointestinal disorder is selected from the group consisting of achalasia, Hirschsprung's disease, congenital pyloric stenosis, reflux disease, irritable bowel syndrome, and intestinal pseudo-obstruction.

10. A method of treating a disorder of the enteric nervous system in a subject suffering from an enteric nervous disorder associated with lower levels of NO comprising implanting isolated embryonic neural stem cells directly into the gastrointestinal alimentary tract of the subjects wherein the implanted embryonic neural stem cells produce NO.

11. The method of claim 10 wherein implanting cells into a gastrointestinal alimentary tract of a subject comprises administering the cells by local injection.

12. The method of claim 10 wherein the cells are implanted into the pylorus.

13. The method of claim 10 wherein said disorder of the enteric nervous system is selected from the group consisting of achalasia, Hirschsprung's disease, congenital pyloric stenosis, reflux disease, irritable bowel syndrome, and intestinal pseudo-obstruction.

14. The method of claim 10 wherein the implanted cells repopulate neurons.

15. The method of claim 10 wherein the gastrointestinal alimentary tract is to mouth, the esophagus, the stomach, or the bowels.

16. The method of claim 10 wherein the implanted neural stem cells further produce substance P.

17. The method of claim 10 wherein the neural stern cells are implanted into the duodenum.

* * * * *

UNITED STATES PATENT AND TRADEMARK OFFICE
CERTIFICATE OF CORRECTION

PATENT NO. : 6,808,702 B2
APPLICATION NO. : 09/834110
DATED : October 26, 2004
INVENTOR(S) : Pankaj J. Pasricha and Maria A. Micci It is certified that error appears in the above-identified patent and that said Letters Patent is hereby corrected as shown below:

At column 10, claim 10, line 25, please delete "subject" and insert --subjects,--.

At column 10, claim 15, line 40, please delete "to mouth" and insert --the mouth--.

At column 10, claim 17, line 44, please delete "stern" and insert --stem--.

Signed and Sealed this

Fifth Day of September, 2006

JON W. DUDAS
*Director of the United States Patent and Trademark Office*